United States Patent
Majer et al.

(10) Patent No.: US 10,077,751 B2
(45) Date of Patent: Sep. 18, 2018

(54) METHOD AND DEVICE FOR CHARACTERIZING AN INJECTOR

(71) Applicant: Robert Bosch GmbH, Stuttgart (DE)

(72) Inventors: Clemens Majer, Ingersheim (DE); Thomas Fischer, Stuttgart (DE); Iris Hartung, Schorndorf (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 15/322,050

(22) PCT Filed: May 8, 2015

(86) PCT No.: PCT/EP2015/060197
§ 371 (c)(1),
(2) Date: Dec. 23, 2016

(87) PCT Pub. No.: WO2015/197252
PCT Pub. Date: Dec. 30, 2015

(65) Prior Publication Data
US 2017/0145975 A1    May 25, 2017

(30) Foreign Application Priority Data
Jun. 27, 2014 (DE) .......................... 10 2014 212 392

(51) Int. Cl.
*G01F 1/34* (2006.01)
*F02M 65/00* (2006.01)
(Continued)

(52) U.S. Cl.
CPC ............ *F02M 65/001* (2013.01); *G01F 1/34* (2013.01); *G01F 1/666* (2013.01); *G01F 1/68* (2013.01);
(Continued)

(58) Field of Classification Search
CPC ....................................................... G01F 1/20
See application file for complete search history.

(56) References Cited

U.S. PATENT DOCUMENTS

| | | | |
|---|---|---|---|
| 7,171,847 B2 * | 2/2007 | Kuhn | F02M 65/001 73/114.48 |
| 7,950,267 B2 * | 5/2011 | Vandyke | F02M 65/005 73/1.16 |
| 2010/0024516 A1 | 2/2010 | Vandyke et al. | |

FOREIGN PATENT DOCUMENTS

| | | |
|---|---|---|
| DE | 10104798 | 8/2002 |
| DE | 102004049002 | 4/2006 |

(Continued)

OTHER PUBLICATIONS

International Search Report for Application No. PCT/EP2015/060197 dated Jul. 30, 2015 (English Translation, 3 pages).

*Primary Examiner* — Jewel V Dowtin
(74) *Attorney, Agent, or Firm* — Michael Best & Friedrich LLP

(57) ABSTRACT

The invention relates to a device for determining the mass of fluid (2) discharged by an injector (13), the device comprising a housing (1) which is impermeable to fluid and which serves for storing fluid, said housing having an injector port (11) for the connection, in particular of an inlet (12), of the injector (13) and having a fluid port (8) for the infeed of fluid (2), wherein at least one pressure sensor (3) for pressure measurement is provided in the housing (1) in order, by way of an evaluation unit (17), to determine the mass of the fluid (2) in the housing (1) in a manner dependent on the determined pressure.

11 Claims, 1 Drawing Sheet

(51) Int. Cl.
  *G01N 29/024* (2006.01)
  *G01F 22/02* (2006.01)
  *G01F 1/66* (2006.01)
  *G01F 1/68* (2006.01)

(52) U.S. Cl.
  CPC ........... *G01F 22/02* (2013.01); *G01N 29/024* (2013.01); *F02D 2200/0614* (2013.01); *G01N 2291/102* (2013.01)

(56) References Cited

FOREIGN PATENT DOCUMENTS

| | | |
|---|---|---|
| DE | 102008040628 | 1/2010 |
| EP | 2192389 | 6/2010 |
| JP | 2012233411 | 11/2012 |

\* cited by examiner

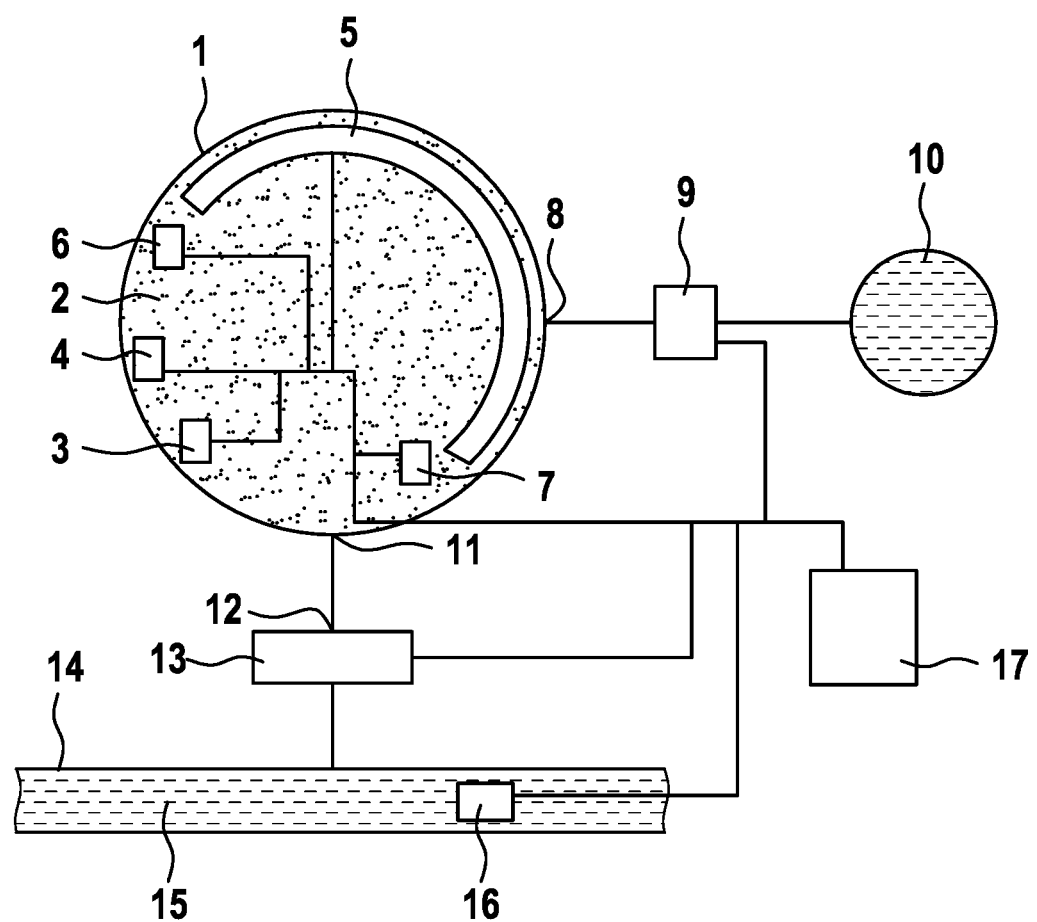

METHOD AND DEVICE FOR CHARACTERIZING AN INJECTOR

BACKGROUND OF THE INVENTION

The invention relates to a device for determining the mass of a fluid delivered by an injector, comprising a fluid-impermeable housing for fluid storage, the latter comprising an injector connection for connection, in particular of an inlet, of the injector and a fluid connection for feeding fluid in. The invention furthermore relates to a plurality of methods for determining the mass of fluid delivered by an injector.

The field of use of the invention extends to the development, functional testing and maintenance of fluid injectors, in particular gas injectors. Such injectors are used, for example, in the injection systems of diesel or petrol engines. One of the essential characteristic parameters of such an injector is the flow rate of fluid during its opening time, during which the fluid flow from the inlet to the outlet of the injector is made possible. The mass delivered per shot of such an injector is given from the opening time and the effective flow resistance of the injector during an injection process, together with the fluid properties, mathematically as an integral of the flow rate over this opening time, and in practice as an amount delivered within an injection process, as a characteristic and essential feature.

In the generally known prior art, measuring instruments based on the Coriolis force are used for flow rate measurement. In these instruments, a fluid flow is passed through a tube mechanically vibrating laterally, the inertia in conjunction with the density and the flow speed of the fluid contained in the tube influencing the resonance properties, particularly in the form of a phase shift along the tube. A corresponding phase offset can then be measured and used in order to quantify the fluid flow.

A disadvantage with this procedure is that the physical working principle requires a fluid flow formed constantly along the tube, or only having variations of orders of magnitude which are very much less than the axial extent of the tube. In the case of injectors whose opening times lie at low temporal orders of magnitude, for example hundredths of seconds or less, it is therefore necessary to generate quasi-homogeneous fluid flows by the respective injector carrying out a multiplicity of injections in rapid succession. The flow rate then measured by the Coriolis measuring instrument may be divided by the number of injections in order to obtain the flow rate, or the amount of fluid of an individual injection. A disadvantage with this is that no information about variation between individual injections (shot-to-shot variation) is possible, although it is precisely this device-specific parameter which is particularly relevant in practice.

SUMMARY OF THE INVENTION

The object of the present invention is to provide a device which makes it possible to determine the amount, or the mass, of the fluid delivered by an injector on a single-shot basis.

The invention includes the technical teaching that at least one pressure sensor for pressure measurement is provided in the housing, in order to determine the mass of the fluid in the housing by means of an evaluation unit on the basis of the pressure determined.

Determination of the mass of the fluid in the housing is used to determine the mass of the fluid which the injector ejects. The mass of the fluid ejected by the injector is the difference between the mass of the fluid which is arranged in the housing before activation of the injector and the mass of the fluid which remains in the housing after the activation. The determination of the mass of the fluid in the housing is in this case carried out by the diagnostics fitted there. For example, in the case of a fluid which approximately obeys the ideal gas equation, it is possible to calculate the number of atoms or molecules in a volume as a function of the volume, the pressure and the temperature. One possible representation form of the ideal gas equation reads, for example, $N=pV/(kT)$ with the fluid particle number N, the pressure p, the volume V, Boltzmann's constant k and the temperature T. The mass of the fluid in the volume then corresponds to the mass, for example known from the technical literature, of an individual particle multiplied by the particle number N. The parameters on the right-hand side of this equation may be determined on a single-shot basis. A single-shot basis means that the measurement can be carried out during a single activation of the injector, instead of being averaged over many activations, as for example in the case of measuring instruments based on the Coriolis force. It is for example possible, by using a pressure sensor, to estimate the fluid particle number when an isothermal system is assumed and the constant temperature is known.

According to one preferred variant of the invention, at least one temperature means for temperature measurement or temperature regulation of the fluid in the housing is additionally provided in the housing. The temperature means may in this case be at least one temperature sensor, which noninvasively delivers information about the temperature in the housing, or at least one temperature regulator, which produces a predefined temperature in the housing. It is also possible to use both embodiments of the temperature means simultaneously.

In order to provide an additional method for determining the amount of fluid, or in order to increase the measurement accuracy, and/or in order to achieve knowledge about further fluid properties, for example the isentropic exponent $[\ ]=[\ ]c^2/p$ (with the measured pressure p, the calculated density $[\ ]$ and the measured speed of sound c), a sound sensor and a sound emitter, preferably operating in the ultrasound range, may be fitted preferably on the inside of the housing, so that sound waves, which propagate through the fluid and are received by the sound sensor, are emitted by the sound emitter.

By the diagnostics comprising the sound emitter and the sound sensor, it is therefore possible to study fluid parameters along one or more paths through the fluid, instead of only locally at a single position, for example as in the case of a temperature sensor geometrically limited to a few cubic millimeters. Local variations of the fluid parameters influencing the sound measurement are therefore automatically averaged by this form of measurement over one or more paths in the fluid. For example, with knowledge of the fluid volume, which when the fluid is in the form of a gas preferably corresponds to the internal volume of the housing, by measuring the speed of sound and with knowledge of the pressure in the housing the density and therefore the mass before and after opening of the injector can be measured computationally in order to determine the mass of fluid delivered from the difference of the two masses.

The sound emitter and the sound receiver may in this case be embodied by a single element, which can both convert electrical signals into sound and convert sound waves into electrical signals.

According to one advantageous embodiment of the invention, a container, for example a tube carrying a flow or a closed container, is fitted on the outlet side of the injector. By definition of the pressure applied on the outlet side of the injector, it is therefore possible to produce a structure intended for testing the injector, which physically corresponds to a structure which is relevant in practice. For example, the pressure or the flow in a cylinder of a piston engine may be simulated there.

The fluid is preferably compressible fluid More preferably the fluid is a gas which can preferably be described well by the ideal gas equation. Relevant examples thereof are air, nitrogen, liquefied petroleum gas, natural gas or a fuel gas.

According to one preferred embodiment of the invention, in addition to the pressure, the evaluation unit also evaluates the measurement values of the temperature sensor and/or sound wave sensor in order to determine the mass of the fluid delivered by the injector. For example, the evaluation unit processes the data of the respective sensors in order to carry out the mass determination of the fluid inside the housing before and after opening of the injector, subsequently takes the difference of these masses and optionally outputs this or transmits it electronically. In this way, the testing or characterization of the injector may optionally be fully automated.

According to a method relating to the invention, in the device described above, an inlet of the injector is connected to the injector connection in order to extract fluid from the housing, after which fluid parameters which make it possible to determine the mass, in particular the mass difference of the fluid arranged in the housing before and after opening of the injector, are recorded in the housing before and after opening of the injector.

This method is further improved in that the injector opens on the outlet side into a container, in particular with a predefined pressure. In this way, it is possible to simulate physically equivalently configurations which are relevant in practice.

According to a further method, an outlet of the injector is connected to the fluid connection, in that this fluid connection thus simultaneously constitutes the injector connection, so that fluid is injected into the housing by the injector in order to allow a determination of the mass there, in particular the mass difference of the fluid arranged in the housing before and after opening of the injector.

BRIEF DESCRIPTION OF THE DRAWING

Further measures which improve the invention are presented in more detail below together with the description of a preferred exemplary embodiment of the invention with the aid of the single FIGURE.

FIG. 1 shows the diagram of a device according to the invention for characterizing an injector.

DETAILED DESCRIPTION

According to the FIGURE, a pressurized fluid 2 in the form of a gas is contained in a housing 1 having an internal volume. Arranged on the inside of the housing 1 there is a pressure sensor 3, a temperature means 4 in the form of a temperature sensor, a further temperature means 5 in the form of a cooling means which cools the fluid 2, a sound wave emitter 6 and a sound wave sensor 7. A fluid connection 8 of the housing is connected to a valve 9, through which pressurized fluid 2 can be fed from a fluid container 10 into the housing 1. The inlet 12 of an injector 13, which opens on the outlet side into a container 14 through which the fluid 15 which is under a preferably predefined pressure flows, is connected to an injector connection 11. A pressure sensor 16 for determining the pressure applied therein is connected in this container 14 in the form of a fluid channel. An evaluation unit 17 controls the injector 13, the sound wave emitter 6, the valve 9 and the temperature means 5 in the form of a cooling means and monitors the values of the pressure sensor 3, the temperature means 4 in the form of a temperature sensor, the sound wave sensor 7 and the pressure sensor 16.

By the structure represented here, before and after opening and subsequent closing of the injector 13, inter alia the pressure, the temperature and the speed of sound in the fluid 2 can be measured, so that computational determination of the fluid 2 delivered from the housing 1 by the injector 13, or its mass, is made possible. The measurement of the pressure of the fluid 15 in the container 14 in the form of the fluid channel by the pressure sensor 16 is not relevant for the determination of the mass of the fluid 2 delivered, and is only used optionally to construct a realistic measurement environment oriented toward a practical scenario.

The invention is not restricted to the exemplary embodiment described above. Rather, variants thereof which are jointly covered by the appended claims are also possible. For example, it is conceivable to select the volume of the container to be so large, or for the period of time during which the injector is open to be so short, that the pressure in the housing changes only marginally and a constant or approximately constant pressure is therefore applied to the inlet of the injector throughout the injection process, in order optionally to achieve a structure physically closer to a case which is relevant in practice.

It is likewise possible, for example, to use only a sound emitter and a sound sensor and a pressure sensor, or only a pressure sensor and a temperature sensor, or only cooling means and a sound emitter and a sound sensor, or any other desired combination of the sensors.

It is likewise conceivable, and therefore jointly covered by the appended claims, that instead of the valve the injector is connected on the inlet side to the fluid container and on the outlet side to the fluid connection, so that fluid is injected by the injector into the housing and not, as represented in the FIGURE, extracted therefrom. As a consequence, the fluid parameters of the fluid delivered into the housing by the injector are determined. In this method, the injector connection is then identical to the fluid connection and, unlike as represented in the FIGURE, it is not the fluid that the injector extracts from the housing which is measured, but the fluid that the injector injects into the housing.

What is claimed is:

1. A device for determining the mass of a fluid (2) delivered by an injector (13), comprising a fluid-impermeable housing (1) for fluid storage, the latter comprising an injector connection (11) configured to be connected to the injector (13) and a fluid connection (8) for feeding fluid (2) in, characterized in that at least one pressure sensor (3) for pressure measurement is provided in the housing (1), in order to determine the mass of the fluid (2) in the housing (1) by means of an evaluation unit (17) on the basis of the pressure determined before and after delivery of fluid (2) by the injector (13), and in that the evaluation unit (17) additionally evaluates the measurement values of a temperature sensor (4) and/or sound wave sensor (7) before and after delivery of fluid (2) by the injector (13) in order to determine the mass of the fluid (2) delivered by the injector (13) on a single-shot basis, and wherein the injector connection (11) is configured to be connected to an inlet (12) of the injector (13).

2. The device as claimed in claim 1, characterized in that at least one temperature means (4; 5) for temperature measurement or temperature regulation of the fluid (2) in the housing (1) is provided in the housing (1).

3. The device as claimed in claim 2, characterized in that the at least one temperature means comprises the temperature sensor (4).

4. The device as claimed in claim 2, characterized in that the at least one temperature means comprises a temperature regulator (5).

5. The device as claimed in claim 1, characterized in that a sound wave emitter (6) and the sound wave sensor (7) are fitted on or in the housing, in order to measure properties of the propagation of sound through the fluid (1) inside the housing (1).

6. The device as claimed in claim 1, characterized in that a container (14) for connection to an outlet of the injector (13) is provided.

7. The device as claimed in claim 1, characterized in that the fluid (2) is a gas from a group of gases to which the air, nitrogen and fuel gas are assigned.

8. A method for determining the mass of fluid (2) delivered by an injector (13) by an inlet (12) of the injector (13) being connected to the injector connection (11) of a device as claimed in claim 1, a fluid (2) being conveyed through the fluid connection (8) into the housing, the pressure of the fluid (2) in the housing (1) being measured by the pressure sensor (3) and read out by the evaluation unit (17), fluid (2) subsequently being delivered from the housing (1) by the injector (13), the pressure of the fluid (2) in the housing (1) subsequently being measured again by the pressure sensor (3) and read out by the evaluation unit (17), and the mass of the fluid (2) in the housing (1) before and after delivery of fluid (2) by the injector (13) being calculated by the evaluation unit (17) by means of the previously determined measurement values on a single-shot basis, and wherein, for this calculation of the mass of the fluid (2) on a single-shot basis, before and after delivery of fluid (2) by the injector (13), the temperature of the fluid (2) is determined by the temperature means (4) and read out by the evaluation unit (17) and/or the speed of sound in the fluid (2) is determined by the sound wave sensor (7) and read out by the evaluation unit (17).

9. The method as claimed in claim 8, characterized in that the fluid (2) is delivered by the injector (13) into a container (14) with a predefined pressure.

10. A method for determining the mass of fluid (2) delivered by an injector (13) by an inlet (12) of the injector (13) being connected to a fluid container (10), the injector being connected on the outlet side to the fluid connection (8) of a device as claimed in claim 1, the pressure of the fluid (2) in the housing (1) being measured by the pressure sensor (3) and read out by the evaluation unit (17), fluid (2) subsequently being delivered into the housing (2) by the injector (13), the pressure of the fluid (2) in the housing (1) subsequently being measured again by the pressure sensor (3) and read out by the evaluation unit (17), and the mass of the fluid (2) in the housing (1) before and after delivery of fluid (2) by the injector (13) being calculated by the evaluation unit (17) by means of the previously determined measurement values on a single-shot basis, and wherein, for this calculation of the mass of the fluid (2) on a single-shot basis, before and after delivery of fluid (2) by the injector (13), the temperature of the fluid (2) is determined by the temperature means (4) and read out by the evaluation unit (17) and/or the speed of sound in the fluid (2) is determined by the sound wave sensor (7) and read out by the evaluation unit (17).

11. The device as claimed in claim 1, characterized in that a sound wave emitter (6) and the sound wave sensor (7) are fitted on or in the housing, in order to measure the speed of sound inside the housing (1).

* * * * *